United States Patent [19]
Haas

[11] 3,932,603
[45] *Jan. 13, 1976

[54] ORAL PREPARATIONS FOR REDUCING THE INCIDENCE OF DENTAL CARIES

[75] Inventor: Gerhard J. Haas, Woodcliff Lake, N.J.

[73] Assignee: General Foods Corporation, White Plains, N.Y.

[ * ] Notice: The portion of the term of this patent subsequent to Mar. 13, 1991, has been disclaimed.

[22] Filed: May 28, 1971

[21] Appl. No.: 148,203

[52] U.S. Cl. .................................. 424/49; 424/57
[51] Int. Cl.² ........................................ A61K 7/16
[58] Field of Search .................... 424/48, 54, 57, 58

[56] References Cited
UNITED STATES PATENTS 2,772,204  11/1956  King ...................................... 424/48
3,309,274  3/1967  Brilliant ................................. 424/57

FOREIGN PATENTS OR APPLICATIONS
1,901,277  8/1970  Germany

OTHER PUBLICATIONS

*Dental Abstracts*, Vol. 9, No. 6, pp. 350 & 351, June 1964.

*Primary Examiner*—Shep K. Rose
*Attorney, Agent, or Firm*—Thomas R. Savoie; Daniel J. Donovan; Bruno P. Struzzi

[57]  ABSTRACT

This invention relates to new and improved oral preparations and particularly to preparations having the effect of inhibiting dental caries in the mouth. This invention has identified a number of compounds which are effective as antimicrobial agents against cariogenic streptococci and which would be effective for use in oral preparations as a means to reduce dental caries.

1 Claim, No Drawings

ORAL PREPARATIONS FOR REDUCING THE INCIDENCE OF DENTAL CARIES

The underlying causes of dental caries are multifaceted. One aspect is the microbiological one. In order for caries to develop, infection by microorganisms has to occur.

During recent years it has been found that the organisms most often associated with the formation of multisurface caries are certain salivary streptococci belonging to the strep mutans group. These multi-surface caries are particularly prevalent in children and young adults; the so-called rampant caries belong to this type. The cariogenic organisms appear to have the special capability of developing a high molecular weight, water-insoluble type of dextran from sucrose. This dextran is believed to be a major constituent of the dental plaque normally associated with dental caries.

Various means have been contemplated for controlling the amount of plaque in the mouth. The use of certain enzymes such as Pancreatin is disclosed in U.S. Pat. No. 3,235,460 as effective to inhibit the formation of dental plaque. Commonly-assigned U.S. Pat. application Serial No. 124,465 filed Mar. 15, 1971 discloses several surface active agents which are also effective to inhibit or reduce the formation of dental plaque.

It has also been proposed to employ direct bactericidal action on the cariogenic microorganisms to assist in the reduction or prevention of dental caries. U.S. Pat. Nos. 2,921,886 and 3,450,812 respectively disclose alkyl morpholine compounds and nitrogen based compounds having an empirical formula of $C_{38}H_{61}NO_{14}$ as antimicrobials which are effective as anticaries agents.

This invention has identified a number of compounds which have been found to be antimicrobial against cariogenic streptococci. These compounds have the apparent ability to either inhibit the growth of or destroy selected cariogenic streptococci.

Coupled with the problem of identifying antimicrobial compounds effective in reducing dental caries is the necessity of finding a means whereby the effective substance may be permitted to act in the mouth. The problem is rendered even more complex by the necessity that the substance possess certain requisite supplementary characteristics such as satisfactory properties from the viewpoint of oral toxicity, acute chronic toxicity, non-sensitization, non-irritation of mucous membranes, etc.

An important feature of this invention is the use of compounds which have low toxicity and which may be readily incorporated into a variety of oral preparations.

Broadly, the present invention relates to an oral preparation for the inhibition of dental caries having as an active ingredient a compound which has been newly found to be antimicrobial against cariogenic streptococci. These preparations can take the form of toothpastes, tooth powders and mouth washes, or the like, but since it is highly desirable to have the active ingredient present in the mouth for extended periods, the preparations may also be in the form of chewing gum or of a lozenge or drop which can be slowly dissolved in the mouth.

The compounds of this invention which have been found to be highly effective as antimicrobials against cariogenic streptococci are sodium tripolyphosphate, sodium hexameta-phosphate, disodium salt of 9-o-carboxyphenyl-6-hydroxy-2, 4, 5, 7-tetraiodo-3-isoxanthone (FD&C Red No. 3), sodium-palmitoyl-L-lysine-L-lysine ethyl ester dihydrochloride, sodium-palmitoyl-L-lysine-L-lysine amide dihydrochloride, hop extract resins (e.g. lupulone and humulone).

Compounds which have shown some activity as antimicrobials against cariogenic streptococci but which are not considered part of this invention are calcium dihydrogenphosphate, sodium phosphate, sodium trimetaphosphate and L-lysine-n-doceyl ester dihydrochloride.

It is also possible to incorporate various adjuvant materials into the oral preparations of this invention. The oral preparation may contain such materials in suitable amounts provided they are compatible with the antimicrobial compounds and the essential properties of the oral preparation.

Added ingredients in the oral preparations may also seek to reduce the incidence of dental caries such as the incorporation of enzymes or other materials which are effective to inhibit the production of dental plaque.

Such materials as sweeteners, flavoring oils, coloring or whitening agents, preservatives, alcohols and the like may be readily incorporated into the oral preparations of this invention. Dentifrice formulations should also contain as a major proportion of the solid ingredients water-insoluble abrasives or polishing agents such as calcium carbonate, tricalcium phosphate, bentonite, etc.

In the preparation of tooth powders it is usually sufficient to mechanically blend the various solid ingredients, including effective amounts of the antimicrobial compound and abrasives, into a homogeneous powder.

Mouth washes or rinses prepared in accordance with this invention will usually comprise an effective amount of the antimicrobial compound dissolved in a suitably flavored liquid vehicle such as an aqueous alcoholic vehicle.

The lozenges or troches contemplated by this invention are prepared by mixing particles of the antimicrobial compound with mucilage and natural or artificial sweeteners and flavoring agents. Gelatin and water is also an effective base for these candy-like products. Chewing gum can be prepared by the substitution of a standard gum base for the mucilage. Suitable bulking agents or fillers may be added to any of these edible products.

The oral preparations of this invention may be prepared in accordance with the skill and practice of the prior art. The distinguishing feature of this invention is the inclusion of an effective amount of selected antimicrobial compounds to reduce the incidence of dental caries. These antimicrobial compounds may be incorporated into the oral preparation either as a substitute for or in addition to other anti-caries agents which have previously been discovered and employed by the prior art.

The antimicrobial compounds or combination of compounds of this invention should be present in the oral preparations in an amount sufficient to produce an effective concentration of the compounds in the mouth. Normally this involves the formation of oral preparations which contain the antimicrobial compound at about 0.002% to 5% by weight; although, it will be readily appreciated by those skilled in the art that the phosphate and FD & C Red No. 3 antimicrobials of this invention will normally be used at the high end of this use range, say 0.3% to 5%, while the dipeptide and the hop extract resin antimicrobials of this invention will normally be used at the low end of the use range, say 0.002% to 0.3%.

The compounds of this invention were shown to be antimicrobial against cariogenic streptococcus by their effect on known cariogenic streptococci. The compounds were tested at various concentrations in a thioglycollate broth medium inoculated with a known amount of cariogenic organisms and were quantitatively compared with control cultures which did not contain the antimicrobial compound. Additional cultures containing equivalent amounts of compounds found to be less effective as antimicrobial against cariogenic streptococci were also investigated; however, these compounds are not considered as part of this invention.

Selected cultures were qualitatively evaluated by comparing the amount of dextran produced during three days of growth. According to the procedure for this test the cariogenic organisms were placed in glass tubes containing Streptococcus Salivarius-Mitis agar (Difco) together with 5% sucrose, a pinch of calcium carbonate (except the antimicrobial compound and control). After 72 hours the insoluble material containing both organisms and dextran was separated by centrifugation and dissolved in cold 1N potassium hydroxide. This solution is then refrigerated for two hours and centrifuged to remove the organisms. The clarified solution is then mixed with sufficient ethanol to bring the alcohol content to 70% by weight and placed in a refrigerator overnight, during which time the dextran precipitates. The precipitated material is separated and the amount of carbohydrate (dextran) is visually compared.

The results are summarized in the Tables below.

Table 1 pH adjusted to 7.2 before inoculation
inoculum: 5×10⁴ (FA-1 organisms/ml.)
period: 24 hours
temperature: 37°C

| compound | concentration (weight %) | final count (FA-1 organisms/ml.) |
|---|---|---|
| control | | $1.2 \times 10^9$ |
| sodium phosphate $Na_3PO_4$ | 1.0 | $6 \times 10^7$ |
| calcium dihydrogenphosphate $Ca(H_2PO_4)_2 \cdot H_2O$ | 1.0 | $2 \times 10^6$ |
| sodium tripolyphosphate $Na_5P_3O_{10}$ | 1.0 | $3 \times 10^3$ |
| sodium hexametaphosphate $Na(PO_3)_6$ | 1.0 | <1 |

Table 2 pH adjusted to 7.0 before inoculation
inoculum: 1×10⁴ (FA-1 organisms/ml.)
temperature: 37°C
period: 24 hours

| compound | concentration (weight %) | final count (organisms/ml) |
|---|---|---|
| control | | $>3 \times 10^9$ |
| sodium hexametaphosphate | 1 | 15 |
| " | 0.3 | $9 \times 10^7$ |
| " | 0.1 | $>3 \times 10^9$ |
| sodium tripolyphosphate | 1 | 32 |
| " | 0.3 | $3 \times 10^8$ |
| " | 0.1 | $2.6 \times 10^9$ |
| calcium dihydrogenphosphate | 1 | $4 \times 10^3$ |
| " | 0.3 | $7 \times 10^7$ |
| " | 0.1 | $2 \times 10^9$ |

Table 3 pH adjusted to 7.0 before inoculation
inoculum: FA-1
period: 3 days
temperature: 37°C

| compound | concentration (weight %) | dextran |
|---|---|---|
| control | | +++ |
| sodium tripolyphosphate | 1.0 | 0 |
| " | 0.1 | ++ |
| calcium dihydrogenphosphate | 1.0 | 0 |
| " | 0.1 | ++ |
| sodium hexametaphosphate | 1.0 | + |
| " | 0.1 | ++++ |
| sodium phosphate | 1.0 | ++ |
| " | 0.1 | ++ |

Table 4 pH adjusted to 7.0 before inoculation
inoculum: 2×10⁴(SL-1 organisms/ml)
period: 24 hours
temperature: 37°C

| compound | concentration (weight%) | final count (organisms/ml) |
|---|---|---|
| control | | $5 \times 10^8$ |
| sodium tripolyphosphate | 1.0 | $3 \times 10^2$ |
| control | | $3 \times 10^5$ |
| sodium dihydrogenphosphate | 1.0 | 0 |
| sodium hexametaphosphate | 1.0 | 0 |
| " | 0.3 | $1 \times 10^4$ |

Table 5 inoculum: 2.1×10³ (FA-1 organisms/ml)
period: 24 hours
temperature: 37°C

| compound | concentration (weight %) | final count (organisms/ml) |
|---|---|---|
| control | | $6 \times 10^8$ |
| FDC Red No. 3 | 1 | $<10^6$ |
| FDC Red No. 3 | 0.1 | $1 \times 10^6$ |
| FDC Red No. 3 | 0.01 | $2.7 \times 10^8$ |

Table 6 inoculum: 3.2×10³ (FA-1 organisms/ml)
period: 48 hours
temperature: 37°C

| compound | concentration (weight %) | final count (organisms/ml) |
|---|---|---|
| control | | $2 \times 10^8$ |
| Na-palmitoyl-L-lysine-L-lysine-ethyl ester dihydrochloride | 0.001 | $<10^4$ |
| Na-palmitoyl-L-lysine-L-lysine amide dihydrochloride | 0.001 | $<10^4$ |
| L-lysine-n-doceyl ester dihydrochloride | 0.1 | $<10^6$ |
| L-lysine-n-doceyl ester dihydrochloride | 0.01 | $1.7 \times 10^5$ |

Table 7

| | | period: 72 hours | |
| --- | --- | --- | --- |
| inoculum: $1\times10^5$ (FA-1 organisms/ml) | | temperature: 37°C | |
| compound | concentration (weight %) | dextran | final count (organisms/ml) |
| control | | +++ | $5 \times 10^8$ |
| hop extract (S.S.Steiner Inc.) | 0.01 | 0 | $9 \times 10^2$ |
| " | 0.005 | + | $8 \times 10^4$ |
| " | 0.001 | ++ | $1 \times 10^5$ |
| " | 0.0005 | ++ | $3 \times 10^6$ |

Table 8

| | | period: 24 hours |
| --- | --- | --- |
| inoculum: $5\times10^7$ (FA-1 organisms/ml) | | temperature: 37°C |
| compound | concentration (weight %) | final count (organisms/ml) |
| control | | $3 \times 10^8$ |
| FDC Red No. 3 | 1 | <1 |
| FDC Red No. 3 | 0.3 | <1 |

EXAMPLE

A chewing gum is prepared having the following composition:

| | grams |
| --- | --- |
| Sucrose | 1239 |
| Chicle Gum Base | 413 |
| Corn Syrup 43° Baume | 314 |
| Glycerol | 15 |
| Flavor, Spearmint | 15 |
| Hop Extract (S.S. Steiner Inc.) | 5.3 |

The ingredients are mixed by softening the gum base for ten minutes at 150°F in a one gallon mixer. The glycerol and corn syrup were added to the base and mixed for five minutes. The sugar and active ingredient were then added and mixing continued for another five minutes. The mixture was then cooled and the flavor was added and mixed for two minutes. The mixture was then formed into sheets and scored into sticks.

The precise mechanism by which the various compounds of this invention either inhibit or destroy the growth of cariogenic streptococci is not precisely known; however, this does not preclude the use of this invention or of variations or modifications thereof.

I claim:

1. A method for reducing the incidence of dental caries comprising placing in the mouth an oral preparation containing from 0.002% to 0.3% by weight of an antimicrobial compound selected from the group consisting of sodium-palmitoyl-L-lysine-L-lysine ethyl ester, sodium-palmitoyl-L-lysine-L-lysine amide dihydrochloride and combinations thereof, said preparation capable of producing an effective concentration of the compound in the mouth to be antimicrobial against cariogenic streptococci.

* * * * *

UNITED STATES PATENT AND TRADEMARK OFFICE
CERTIFICATE OF CORRECTION

PATENT NO. : 3,932,603
DATED : January 13, 1976
INVENTOR(S) : Gerhard J. Haas

It is certified that error appears in the above-identified patent and that said Letters Patent are hereby corrected as shown below:

Column 2, lines 1, 2 and 8 (both instances), "sodium" should read -- $N\alpha$ -- .

Column 4, lines 60 and 62, "Na-" should read -- $N\alpha$ -- .

Column 6, lines 24 and 25, "sodium-" should read -- $N\alpha$ -- .

Signed and Sealed this

Tenth Day of August 1976

[SEAL]

Attest:

RUTH C. MASON
*Attesting Officer*

C. MARSHALL DANN
*Commissioner of Patents and Trademarks*